(12) United States Patent
Rabe

(10) Patent No.: US 11,737,859 B2
(45) Date of Patent: Aug. 29, 2023

(54) METHOD FOR PRODUCING A DENTAL PROSTHESIS PART, AND DENTAL PROSTHESIS PART

(71) Applicant: SIRONA DENTAL SYSTEMS GMBH, Bensheim (DE)

(72) Inventor: Susanne Rabe, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 210 days.

(21) Appl. No.: 16/766,339

(22) PCT Filed: Nov. 23, 2018

(86) PCT No.: PCT/EP2018/082446
§ 371 (c)(1),
(2) Date: May 22, 2020

(87) PCT Pub. No.: WO2019/101967
PCT Pub. Date: May 31, 2019

(65) Prior Publication Data
US 2020/0375704 A1    Dec. 3, 2020

(30) Foreign Application Priority Data
Nov. 23, 2017 (DE) .......................... 102017221002.8

(51) Int. Cl.
*A61C 13/00* (2006.01)
*A61C 13/271* (2006.01)
(Continued)

(52) U.S. Cl.
CPC ...... *A61C 13/0004* (2013.01); *A61C 13/0019* (2013.01); *A61C 13/26* (2013.01);
(Continued)

(58) Field of Classification Search
CPC .................................................. A61C 13/0019
See application file for complete search history.

(56) References Cited

U.S. PATENT DOCUMENTS

| 7,024,770 B2 * | 4/2006 | Sun | A61K 6/893 |
| | | | 433/167 |
| 10,363,116 B2 * | 7/2019 | Boronkay | A61C 7/36 |

(Continued)

FOREIGN PATENT DOCUMENTS

| DE | 19950284 A1 | 4/2001 |
| EP | 2450000 A1 | 5/2012 |

(Continued)

OTHER PUBLICATIONS

International Search Report; PCT/ EP2018/082446; Jan. 24, 2019 (completed); Feb. 5, 2019 (dated).

(Continued)

*Primary Examiner* — Jacob J Cigna
(74) *Attorney, Agent, or Firm* — DENTSPLY SIRONA INC.

(57) ABSTRACT

The invention relates to a dental prosthesis part production method, wherein: a dental prosthesis part model is generated taking into account a dental model; a load analysis of the dental prosthesis part model is carried out; a first reinforcing structure model having a first shape and position is arranged inside the dental prosthesis part model and the dental prosthesis part model is reduced by a volume corresponding to the arranged first reinforcing structure model; the reduced dental prosthesis part model is divided into a lower partial volume and an upper partial volume; a lower part of the dental prosthesis part is produced from a first composite material according to the lower partial volume by means of the 3D printer; a first reinforcing structure corresponding to the first reinforcing structure model is arranged on the first part of the dental prosthesis part; and, by means of the 3D (Continued)

printer using the first composite material, an upper part of the dental prosthesis part according to the upper partial volume is placed onto the lower part of the dental prosthesis part comprising the arranged first reinforcing structure.

14 Claims, 2 Drawing Sheets

(51) Int. Cl.
*B33Y 10/00* (2015.01)
*B33Y 50/02* (2015.01)
*B33Y 80/00* (2015.01)
*G05B 19/4099* (2006.01)
*G06Q 50/04* (2012.01)
*G16H 50/50* (2018.01)

(52) U.S. Cl.
CPC ............... *B33Y 10/00* (2014.12); *B33Y 50/02* (2014.12); *B33Y 80/00* (2014.12); *G05B 19/4099* (2013.01); *G16H 50/50* (2018.01); *G05B 2219/49023* (2013.01); *G06Q 50/04* (2013.01)

(56) References Cited

U.S. PATENT DOCUMENTS

| | | | |
|---|---|---|---|
| 10,603,142 B2 * | 3/2020 | Ueno | A61C 13/0004 |
| 11,013,583 B2 * | 5/2021 | Sun | A61C 13/0013 |
| 2006/0131770 A1 * | 6/2006 | Dierkes | A61C 13/0003 |
| | | | 264/16 |
| 2007/0050074 A1 | 3/2007 | Holzner | |
| 2014/0265034 A1 * | 9/2014 | Dudley | B29C 64/106 |
| | | | 264/401 |
| 2017/0007359 A1 * | 1/2017 | Kopelman | G05B 19/4097 |

FOREIGN PATENT DOCUMENTS

| | | |
|---|---|---|
| GB | 2148872 A | 6/1985 |
| WO | 2009090214 A2 | 7/2009 |
| WO | 2011017113 A2 | 2/2011 |
| WO | WO-2017007964 A1 * 1/2017 ............. A61C 7/002 |

OTHER PUBLICATIONS

Written Opinion of the International Searching Authority; PCT/EP2018/082446; Jan. 24, 2019 (completed); Feb. 5, 2019 (dated).
International Preliminary Report on Patentability; PCT/EP2018/082446; Jan. 24, 2019 (completed); Feb. 5, 2019 (dated).

* cited by examiner

METHOD FOR PRODUCING A DENTAL PROSTHESIS PART, AND DENTAL PROSTHESIS PART

TECHNICAL FIELD

The invention relates to a method for producing a dental prosthesis part and a dental prosthesis part.

BACKGROUND OF THE INVENTION

Larger permanent dental prosthesis parts, such as permanent bridge appliances, are typically made of particularly strong materials such as zirconium oxide or a metal.

So-called dental composites are easier to process and less expensive, but are not suitable for the production of permanent bridge appliances because of their physical properties.

To nonetheless be able to utilize the advantages of composite materials, the production of a dental bridge construction from a composite material and a reinforcing glass fiber is known from the article "Clinical and laboratory procedures to fabricate fiber-reinforced composite fixed partial dentures", G. Rappelli et al., Cosmetic Dentistry, No. 4, 2008, wherein a casting mold is filled with the composite material and layers of glass fibers, and the composite material is cured by photopolymerization.

There are also so-called fiber reinforced composites for dental applications, e.g. everX Posterior of GC Corporation, Tokyo, Japan. The material primarily consists of a polymer matrix and short glass fibers as a filler and, according to the manufacturer's specifications, is suitable for filling larger cavities. As is typical for dental composites, the material is introduced into the cavity in layers and cured by polymerization.

With that in mind, the object of the present invention is to further develop the state of the art and provide a production method for a dental prosthesis part that is as reliable and cost-effective as possible as well as a strong and cost-effective dental prosthesis part.

SUMMARY OF THE INVENTION

The method according to the invention is directed toward the production of a dental prosthesis part using a 3D printer, wherein a three-dimensional digital dental prosthesis part model is produced with the aid of a computer and taking into account a digital dental model, the digital dental model includes a toothed and/or untoothed region of a lower jaw and/or upper jaw to be treated, and a load analysis of the dental prosthesis part model is carried out with the aid of a computer and taking into account the dental model.

Taking into account a result of the load analysis, a three-dimensional digital first reinforcing structure model having a first three-dimensional shape and a first position is arranged inside the dental prosthesis part model with the aid of a computer, the dental prosthesis part model is reduced by a volume corresponding to the arranged first reinforcing structure model and the dental prosthesis part model is divided into a lower partial volume and an upper partial volume, wherein the lower partial volume and the upper partial volume respectively adjoin the arranged first reinforcing structure model.

A lower part of the dental prosthesis part is produced from a composite material according to the lower partial volume of the dental prosthesis part model using a 3D printer, a first reinforcing structure corresponding to the first reinforcing structure model is arranged on the first part of the dental prosthesis part and, by means of the 3D printer using the first composite material, an upper part of the dental prosthesis part according to the upper partial volume of the dental prosthesis part model is placed onto the lower part of the dental prosthesis part comprising the arranged first reinforcing structure to complete the dental prosthesis part.

According to one further development, at least one further reinforcing structure model having a further shape and a further position is arranged above and/or next to the first reinforcing structure model inside the dental prosthesis part model with the aid of a computer, the dental prosthesis part model is reduced by the volumes corresponding to the arranged first reinforcing structure model and the at least one further reinforcing structure model and the reduced dental prosthesis part model is divided into a lower partial volume and an upper partial volume and, for each further reinforcing structure model positioned above the first reinforcing structure, into a further middle partial volume. One part of the dental prosthesis part at a time is incrementally produced according to one of the partial volumes by means of a 3D printer using a composite material, and a reinforcing structure corresponding to one of the reinforcing structure models is arranged at the respective position.

The dental model is produced from two-dimensional or three-dimensional images, for example; e.g. using an intraoral camera. It goes without saying that the dental model includes the information about the region to be treated that is necessary for the treatment; e.g. the contours of adjacent teeth, preparation sites, implants with abutments. The dental prosthesis part model is produced manually by means of a suitable input means or automatically. For example, one model tooth or several model teeth from a tooth database are positioned virtually at one or several defects in the dental model, if necessary adjusted in size, and augmented by structures that correspond to the preparation sites and/or prepared regions on adjacent teeth.

According to a first embodiment, the load analysis is carried out using a finite element method. It goes without saying that, for the load analysis, the dental model advantageously includes teeth adjacent and/or opposite to the jaw region to be treated. In a further development, the temporomandibular joint, or a movement of the temporomandibular joint or a chewing movement, is included in the dental model as well and also used in the load analysis. In this way, not only the geometry of the dental prosthesis part itself, but also the influences of the subsequent environment can be taken into account as a part of the load analysis.

Based on the results of the load analysis, a reinforcing structure or a virtual model of the reinforcing structure or, according to the further development also two or more reinforcing structure models, is/are positioned automatically inside the dental prosthesis part directly by the computer and/or manually by a user.

According to a first embodiment, a three-dimensional digital fiber bundle model is arranged as the reinforcing structure model, wherein the shape of the fiber bundle model has a length and a diameter. Between the printing of the lower and the upper part of the dental prosthesis part, a fiber bundle corresponding to the fiber bundle model in length and diameter is arranged on the first part of the dental prosthesis part.

Alternatively, the reinforcing structure is formed from a short fiber-reinforced composite material and produced by means of the 3D printer. For this purpose, the reinforcing structure model is digitally planned with a shape and position and, between the production of the lower and the upper part of the dental prosthesis part, a reinforcing structure corresponding to the model is printed from the short fiber-reinforced composite material. To do this, the 3D printer has an additional nozzle, for example.

A standard dental composite is used as the first composite material. Typical composite materials consist of an organic plastic matrix that is mixed with inorganic filling bodies. In a preferred embodiment, a mass fraction of the organic plastic matrix of the first composite material is at most 40% and a mass fraction of the inorganic filling body is at least 60%.

The first composite material is solidified layer by layer by means of the 3D printer, for example, to produce the respective parts of the dental prosthesis part. According to a preferred further development, the solidification takes place via photopolymerization, i.e. by means of light input with a suitable radiation source.

Using the at least one reinforcing structure, comprising a fiber bundle or a short fiber-reinforced composite, the dental prosthesis part, which otherwise consists of a standard composite material, is provided with a high degree of stability. The method according to the invention can therefore also be used to produce larger bridge appliances and/or permanent dental prostheses.

One advantage of the method according to the invention is that the use of the 3D printer makes production particularly simple, inexpensive and fast. Subdividing the dental prosthesis part model makes simple, incremental and fast production using the 3D printer possible.

It goes without saying that positioning a reinforcing structure embodied as a fiber bundle on the first produced part of the dental prosthesis part is particularly reliable if the first partial volume already extends partially around the volume area accommodating the reinforcing structure. According to one further development, the lower partial volume and/or each middle partial volume comprises at least one recess for accommodating the first or a further reinforcing structure.

It furthermore goes without saying that, in order to avoid damage to the already produced first part of the dental prosthesis part when positioning the fiber bundle in the case of a fiber bundle as the reinforcing structure, the first partial volume should not yet extend too far around the volume area accommodating the reinforcing structure. If the reinforcing structure is embodied as a fiber bundle, it is accordingly advantageous, if the first partial volume is formed without undercuts. If the at least one reinforcing structure is embodied as a fiber bundle, it is particularly preferable to divide the dental prosthesis part model reduced by the at least one reinforcing structure into partial volumes such that none of the partial volumes have undercuts in regions adjacent to one of the reinforcing structures.

Another advantage of the production method according to the invention is that it is very reliable, quick and easy to carry out and results in a very stable and cost-effective dental prosthesis part.

The dental model is advantageously calculated using a plurality of two-dimensional optical images. A simple way of capturing a patient's dental situation is to measure it using an intraoral camera, whereby the camera produces a plurality of two-dimensional images, for example. A three-dimensional model of the measured dental situation, i.e. a dental model, can then be produced in a known manner from said images.

Advantageously, the composite material is biocompatible. The composite material is thus suitable for use in a dental treatment.

The dental prosthesis part is advantageously printed using a photopolymerization process and the composite material contains initiators and stabilizers for the photopolymerization process.

The at least one reinforcing structure embodied as a fiber bundle advantageously comprises glass fibers or carbon fibers or ceramic fibers or fibers made of aluminum oxide or a combination of different fibers. Alternatively or as a further development, the at least one fiber bundle comprises a plurality of fibers embedded in a biocompatible material matrix, wherein, according to one further development, the matrix consists of an organic resin and/or initiators and stabilizers for a photopolymerization process.

The thickness of the at least one reinforcing structure embodied as a fiber bundle model is advantageously selected from a predetermined set of thicknesses, which ensures that a fiber bundle corresponding to the fiber bundle model is present. Fiber bundles are typically available in specific thicknesses, or thicknesses that cannot be adjusted as needed. The length, on the other hand, can be shortened as needed and can thus be adapted to the fiber bundle model. The matrix creates a so-called fiber composite material. The possible combinations of fiber material and matrix material result in many degrees of freedom for configuring the reinforcing structure, referred to here as a fiber bundle. A further subject matter of the invention is a dental prosthesis part, wherein the dental prosthesis part was printed entirely or in part using a 3D printer using an above-described method.

Yet another subject matter of the invention is a dental prosthesis part, wherein the dental prosthesis part was printed entirely or in part using a 3D printer and wherein the dental prosthesis part consists of a first composite material and comprises at least one first reinforcing structure consisting of a fiber bundle or a short fiber-reinforced composite material. The dental prosthesis part is also preferably produced using the above-described method.

The advantages discussed with regard to the method according to the invention also apply accordingly to the dental prosthesis part according to the invention.

BRIEF DESCRIPTION OF THE DRAWINGS

Design examples of the invention are shown in the drawing. The figures show.

DETAILED DESCRIPTION OF THE INVENTION

Figure 1:
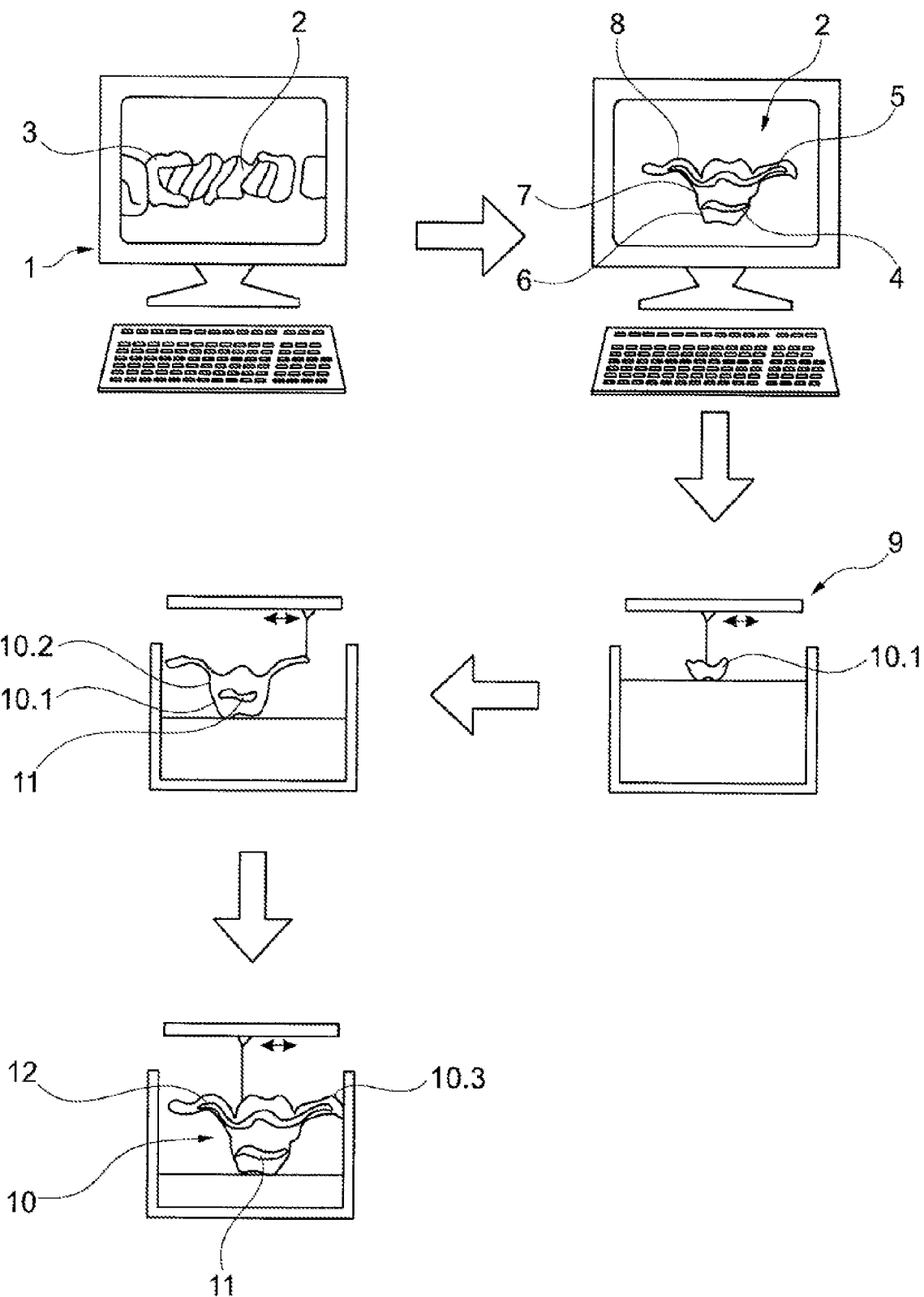
FIG. 1 a schematic sequence of a first embodiment of the production method according to the invention, FIG. 2 a schematic view of a first embodiment of a dental prosthesis part according to the invention, FIG. 3 a schematic view of a second embodiment of a dental prosthesis part according to the invention.

FIG. 1 shows six method steps according to a first embodiment according to the invention of a production method for a dental prosthesis part 10.

Using a computer unit 1, a three-dimensional digital dental prosthesis part model 2 is produced and a load analysis is carried out. A digital dental model 3, which includes a toothed and/or untoothed region of a lower jaw and/or upper jaw to be treated, is used for the design or production of the dental prosthesis part model 2, as well as for the load analysis of the dental prosthesis part model 2. The dental prosthesis part model 2 is planned into the dental model 3 and/or adapted to the dental model 3. According to a first embodiment, the dental prosthesis part model 2 is positioned in the dental model for the load analysis and, among other things, a chewing movement is simulated.

Based on the results of the load analysis, in the depicted design example, an upper and a lower three-dimensional digital reinforcing structure model 4, 5 are arranged inside the dental prosthesis part model 2 with the aid of a computer. The number, the respective three-dimensional shape and the respective position of the reinforcing structure models 4, 5 is determined fully automatically by the computer unit 1 or entirely manually by a user using a suitable input means, or by a combination of automatic steps, e.g. suggestions for position and shape, and manual steps, e.g. optional change of position or shape.

The dental prosthesis part model 2 is then reduced by a volume corresponding to the arranged reinforcing structure model 4, 5, i.e. by the volume areas occupied by the reinforcing structure models 4, 5, and divided into a lower partial volume 6, a middle partial volume 7 and an upper partial volume 8, wherein the lower partial volume 6 extends from a lower surface of the partial volume 6 to the lower reinforcing structure model 4, the middle partial volume 7 extends from the lower reinforcing structure model 4 to the upper reinforcing structure model 5 and the upper partial volume 8 extends from the upper reinforcing structure model 5 to a second surface of the dental prosthetic model 2 opposite to the first surface. The dental prosthesis model 2 is respectively divided along the extension of the reinforcing structure models 4, 5.

The dental prosthesis part 10 is then produced in a number of steps. First a lower part 10.1 of the dental prosthesis part 10 is produced from a composite material according to the lower partial volume 6 of the dental prosthesis part model 2 using a 3D printer 9. This is followed by the arrangement of the lower reinforcing structure model 4.

If the reinforcing structure model 4 is planned or designed as a fiber bundle model according to a first embodiment, a first fiber bundle corresponding in shape to the reinforcing structure model 4, i.e. in particular with respect to length and thickness, is arranged as the lower reinforcing structure 11 on the first part 10.1 of the dental prosthesis part 10 at the position planned for the lower reinforcing structure model 4.

If the reinforcing structure 11 is to consist of a short fiber-reinforced composite in accordance with a second embodiment, a body made of the short fiber-reinforced composite material and corresponding to the three-dimensional shape of the reinforcing structure model 4 is arranged as the lower reinforcing structure 11 at the position planned for the lower reinforcing structure model 4. According to a first option, such a reinforcing structure 11 is produced in advance or in parallel, e.g. using a further 3D printer, and then arranged on the lower part 10.1 of the dental prosthesis part 10. Alternatively, the reinforcing structure 11 is produced directly on the lower part 10.1 of the dental prosthesis part 10 using the same 3D printer.

A middle part 10.2 of the dental prosthesis part 10 is then placed onto the lower part 10.1 of the dental prosthesis part 10 and the lower reinforcing structure 11 by means of the 3D printer 9 using the first composite material according to the middle partial volume 7.

An upper reinforcing structure 12 corresponding to the upper reinforcing structure model 5 is arranged on the middle part 10.2 of the dental prosthesis part 10 at the position planned for the upper reinforcing structure model 5. For this purpose, a fiber bundle corresponding to the upper reinforcing structure model 5 is preferably positioned, or a shape corresponding to the upper reinforcing structure model 5 is produced at the planned position from a short fiber-reinforced composite material by means of the 3D printer.

By means of the 3D printer 9 using the first composite material, an upper part 10.3 of the dental prosthesis part 10 according to the upper partial volume 8 of the dental prosthesis part model 2 is placed onto the middle part 10.2 of the dental prosthesis part 10 comprising the arranged first reinforcing structure 12.

It goes without saying that, to produce a dental prosthesis part 10 with only one first reinforced fiber bundle 4, the dental prosthesis part model 2 is divided only along the first fiber bundle 4 into a lower partial volume 6 and an upper partial volume 8, so that the upper partial volume 8 adjoins the first fiber bundle 4 as well and the upper part 10.3 of the dental prosthesis part 10 is placed directly on the lower part 10.2 with the arranged first reinforcing structure 11 according to the upper partial volume 8.

If more than two reinforcing structure models 4, 5 are arranged in the dental prosthesis part model 2 for reinforcement, the dental prosthesis part model is divided into correspondingly more than three partial volumes, whereby a further middle partial volume and a corresponding production step with printing and arranging or producing the further reinforcing structure is added with each further fiber bundle.

Figure 2:
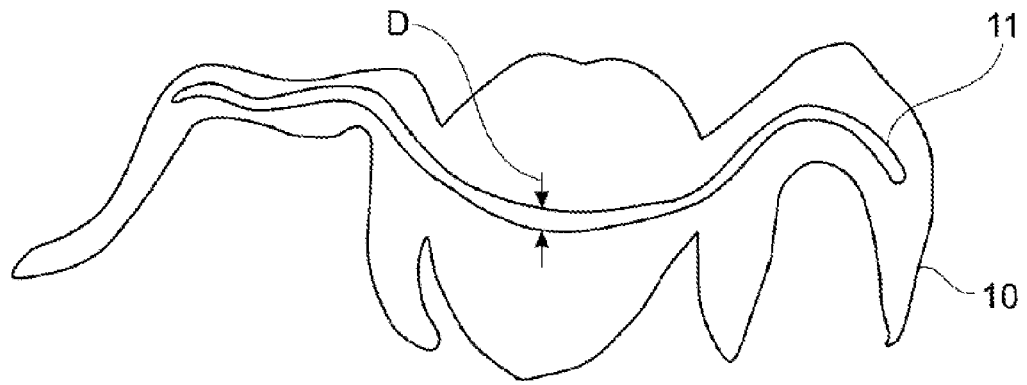

FIG. 2 schematically shows a first embodiment of a dental prosthesis part 10 according to the invention. The dental prosthesis part 10 is embodied as a three-part bridge having a single glass fiber insert as the reinforcing structure 11. The bridge 10 is printed from a composite material using a 3D printer. The glass fiber bundle 11 having a thickness D extends inside the bridge parallel to an entire top upper side of the bridge 10. According to one further development, a definable minimum distance of the glass fiber bundle 11 to every outer surface of the dental prosthesis part 10, for example to the upper side of the bridge 10, ensures that the fiber bundle is always covered by a sufficiently thick layer of composite material.

Figure 3:
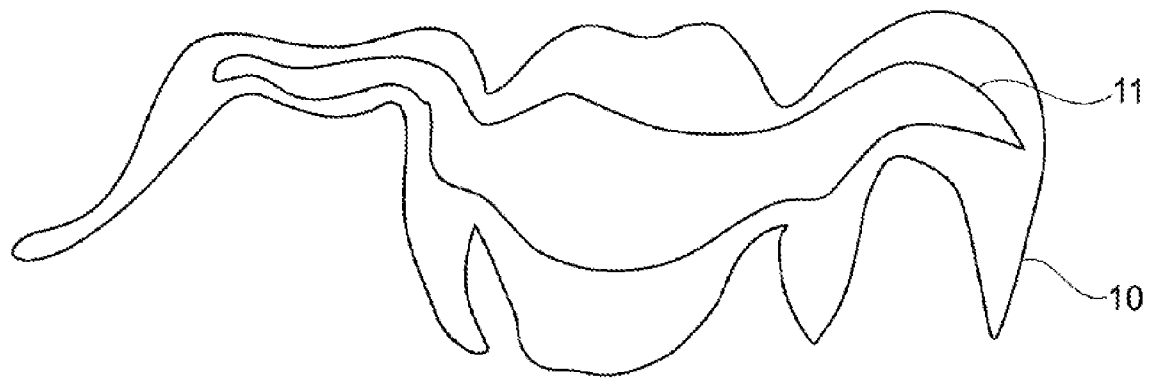

FIG. 3 schematically shows a second embodiment of a dental prosthesis part 10 according to the invention. The dental prosthesis part 10 is embodied as a three-part bridge having a single reinforcing structure 11 made of a short fiber-reinforced composite material.

The invention claimed is:

1. Method for producing a dental prosthesis part using a 3D printer, comprising the steps of:
producing a three-dimensional digital dental prosthesis part model with the aid of a computer and taking into account a digital dental model, wherein the digital dental model includes a toothed and/or untoothed region of a lower jaw and/or upper jaw to be treated,
carrying out a load analysis of the dental prosthesis part model, to automatically compute a three dimensional shape and a first position of a three-dimensional digital first reinforcing structure model, the load analysis being carried out with the aid of a computer and taking into account the dental model by positioning the dental prosthesis part model in the dental model and performing a chewing movement or a movement of the temporomandibular joint, the load analysis further being based on teeth adjacent and/or opposite to a jaw region being treated,
automatically arranging, based on a result of the load analysis, the three-dimensional digital first reinforcing structure model having the first three-dimensional shape and the first position inside the dental prosthesis part model with the aid of a computer and reducing the dental prosthesis part model by a volume corresponding to that of the arranged first reinforcing structure model, dividing the reduced dental prosthesis part model into a lower partial volume and an upper partial volume, wherein the lower partial volume and the upper partial volume respectively adjoin the arranged first reinforcing structure model, producing a lower part of the dental prosthesis part from a first composite material according to the lower partial volume of the dental prosthesis part model using the 3D printer, arranging a first reinforcing structure corresponding to the first reinforcing structure model on the first part of the dental prosthesis part in accordance with the first position, and by means of the 3D printer using the first composite material, placing an upper part of the dental prosthesis part according to the upper partial volume of the dental prosthesis part model onto the lower part of the dental prosthesis part comprising the arranged first reinforcing structure to complete the dental prosthesis part.

2. Method according to claim 1, wherein the load analysis is carried out using the finite element method.

3. Method according to claim 1, wherein the dental model is calculated using a plurality of two-dimensional optical images.

4. Method according to claim 1, wherein the first composite material is biocompatible.

5. Method according to claim 1, wherein the first composite material includes an organic plastic matrix and inorganic filling bodies, wherein a mass fraction of the organic plastic matrix is at most 40% and a mass fraction of the inorganic filling bodies is at least 60%.

6. Method according to claim 1, wherein the dental prosthesis part is printed using a photopolymerization process and the first composite material includes initiators and stabilizers for the photopolymerization process.

7. Method according to claim 1, wherein at least one fiber bundle comprises glass fibers or carbon fibers or ceramic fibers or fibers made of aluminum oxide or a combination of different fibers.

8. Method according to claim 1, wherein the thickness of the at least one fiber bundle model is selected from a predetermined set of thicknesses.

9. Method according to claim 1, wherein the reinforcing structure is produced from a short fiber-reinforced composite material using the 3D printer.

10. Method according to claim 1, wherein the first reinforcing structure model is embodied as a three-dimensional digital fiber bundle model, the shape of the first reinforcing structure model has a thickness and a length, and a fiber bundle corresponding to the three-dimensional digital fiber bundle model is arranged as a reinforcing structure on the lower part of the dental prosthesis part or a middle part of the dental prosthesis part, and further comprising dividing the reduced dental prosthesis part model into partial volumes in such a way that none of the partial volumes have undercuts in regions adjacent to one of the reinforcing structure models, and maintaining a defined minimum distance from the fiber bundle to every outer surface of the dental prothesis part to ensure that the fiber bundle is covered by a sufficiently thick layer of the first composite material.

11. Method according to claim 1, further comprising the steps of arranging at least one further reinforcing structure model having a further shape and a further position above and/or next to the first reinforcing structure model inside the dental prosthesis part model with the aid of a computer, reducing the dental prosthesis part model by the volumes corresponding to the arranged first reinforcing structure model and the at least one further reinforcing structure model, dividing the reduced dental prosthesis part model into a lower partial volume and an upper partial volume and, for each further reinforcing structure model positioned above the first reinforcing structure, into a further middle partial volume, one part of the dental prosthesis part at a time is incrementally produced from the first composite material by means of a 3D printer according to one of the partial volumes, and a reinforcing structure corresponding to one of the reinforcing structure models is arranged at the respective position.

12. Method according to claim 11, wherein the lower partial volume comprises at least one recess for accommodating the first reinforcing structure model and/or said further middle partial volume comprises at least one recess for accommodating a further reinforcing structure model.

13. Method according to claim 1, wherein the at least one fiber bundle comprises a plurality of fibers embedded in a matrix of biocompatible material.

14. Method according to claim 13, wherein the matrix includes an organic resin and/or initiators and stabilizers for a photopolymerization process.

* * * * *